(12) United States Patent
Al Malki (10) Patent No.: US 9,629,401 B2
(45) Date of Patent: Apr. 25, 2017

(54) FACE MASK SYSTEM (71) Applicant: Khalid Hassan Al Malki, Riyadh (SA)

(72) Inventor: Khalid Hassan Al Malki, Riyadh (SA)

(*) Notice: Subject to any disclaimer, the term of this patent is extended or adjusted under 35 U.S.C. 154(b) by 1097 days.

(21) Appl. No.: 13/775,807

(22) Filed: Feb. 25, 2013

(65) Prior Publication Data
US 2014/0237695 A1    Aug. 28, 2014

(51) Int. Cl.
*A62B 18/08* (2006.01)
*A41D 13/11* (2006.01)

(52) U.S. Cl.
CPC .......... *A41D 13/11* (2013.01); *A41D 13/1192* (2013.01); *A62B 18/08* (2013.01)

(58) Field of Classification Search
CPC ............ A41D 13/1192; A41D 13/1115; A41D 13/1146; A41D 13/1161; A41D 2400/36; A41D 13/11; A41D 13/1176; A41D 2300/32; A41D 2400/10; A61M 16/06; A61M 2205/59; A61M 15/08; A61M 16/0683; A61M 2016/0661; A61M 2205/588
USPC ............ 128/206.19, 206.12, 203.29, 204.13, 128/206.13, 857, 202.15, 205.25, 205.27, 128/206.17, 206.21, 206.24, 206.26, 128/206.28, 206.29, 863; 2/9, 171.2, 174, 2/206, 424
See application file for complete search history.

(56) References Cited

U.S. PATENT DOCUMENTS

| | | | |
|---|---|---|---|
| 4,503,851 A | 3/1985 | Braunroth | |
| 4,520,509 A | 6/1985 | Ward | |
| 4,790,307 A | 12/1988 | Haber | |
| 5,243,708 A | 9/1993 | Vanuch | |
| 5,467,765 A | 11/1995 | Maturaporn | |
| 5,538,013 A | 7/1996 | Brannon | |
| 5,636,628 A | 6/1997 | Barnum | |
| 5,891,508 A | 4/1999 | Barnum | |
| 6,758,215 B2 | 7/2004 | Begum | |
| 6,779,524 B2 | 8/2004 | Strawder | |
| 7,004,167 B2* | 2/2006 | Cheng | A41D 13/1192 128/205.27 |
| 7,077,137 B2* | 7/2006 | Russell | A41D 13/1184 128/201.12 |
| 7,311,105 B2 | 12/2007 | Plummer, Jr. | |
| 7,802,572 B2 | 9/2010 | Hahne | |
| 8,240,302 B1* | 8/2012 | Tayebi | A62B 18/08 128/201.15 |
| 2009/0126064 A1* | 5/2009 | Reaux | A41D 13/1161 2/15 |
| 2011/0079225 A1* | 4/2011 | Vole | A41D 13/11 128/206.24 |
| 2012/0090616 A1 | 4/2012 | Means | |
| 2012/0144556 A1* | 6/2012 | Fiebel | A41D 13/11 2/206 |

\* cited by examiner

*Primary Examiner* — Lynne Anderson
*Assistant Examiner* — Elliot S Ruddie
(74) *Attorney, Agent, or Firm* — Donald J. Ersler (57) ABSTRACT

A face mask system for effectively dispensing a medication and/or scented material to a user. The face mask system generally includes a face mask with a medication and/or scented material that is dispensed to a wearer of the face mask via the air breathed into the respiratory system. The medication is dispensed via a medicated cover that is removably attached to the face mask. Alternatively, medicated strips are attached to the face mask to dispense the medication to the wearer of the face mask. One or more deflectors are attached to an upper portion of the face mask to deflect the medication from contacting the eyes of the wearer when worn at daytime.

8 Claims, 15 Drawing Sheets

FACE MASK SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a face mask and more specifically it relates to a face mask system for effectively dispensing a medication to a user.

Description of the Related Art

Any discussion of the related art throughout the specification should in no way be considered as an admission that such related art is widely known or forms part of common general knowledge in the field.

Face masks (a.k.a. surgical masks, procedure masks, dental masks, isolation masks) have been utilized in the medical industry to prevent the spread of disease to patients by health professionals during surgery. Recently, face masks have been utilized by individuals with an illness (e.g. flu, cold) to prevent the spread of the illness to others and/or to prevent the wearer from contracting a disease from another. A conventional face mask is a loose-fitting, disposable device that creates a physical barrier between the mouth and nose of the wearer. Many face masks include ear loops that fit upon the ears of the wearer. When worn properly, a face mask blocks the passage of liquid droplets, splashes, splatter, sprays and aerosols released from the wearer's mouth and nose that contain germs (viruses and bacteria) to prevent the spread of the illness to others. A face mask also prevents the entry of germs into the respiratory system of the wearer.

While face masks are suitable for their intended purpose of blocking germs from exiting or entering a wear, commercially available face masks do not provide the ability to dispense medication to a wearer to help alleviate some of the illness symptoms. Because of the inherent problems with the related art, there is a need for a new and improved face mask system for effectively dispensing a medication to a user.

BRIEF SUMMARY OF THE INVENTION

The invention generally relates to a face mask system which includes a face mask with a medication that is dispensed to a wearer of the face mask via the air breathed into the respiratory system. The medication is dispensed via a medicated cover that is removably attached to the face mask. Alternatively, medicated strips are attached to the face mask to dispense the medication to the wearer of the face mask. Transparent deflectors are attached to the upper portion of the face mask to deflect the medication vapor from contacting the eyes of the wearer when worn at daytime.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview.

Turning now descriptively to the drawings, in which similar reference characters denote similar elements throughout the several views, FIGS. 1 through 10b illustrate a face mask system 10, which comprises a face mask 20 with a medication that is dispensed to a wearer of the face mask 20 via the air breathed into the respiratory system. The medication is dispensed via a medicated cover 30 that is removably attached to the face mask 20. Alternatively, medicated strips 50 are attached to the face mask 20 to dispense the medication to the wearer of the face mask 20. One or more deflectors are attached to the upper portion of the face mask 20 to deflect the medication vapor from contacting the eyes of the wearer when worn at daytime.

B. Face Mask.

Figure 1A:
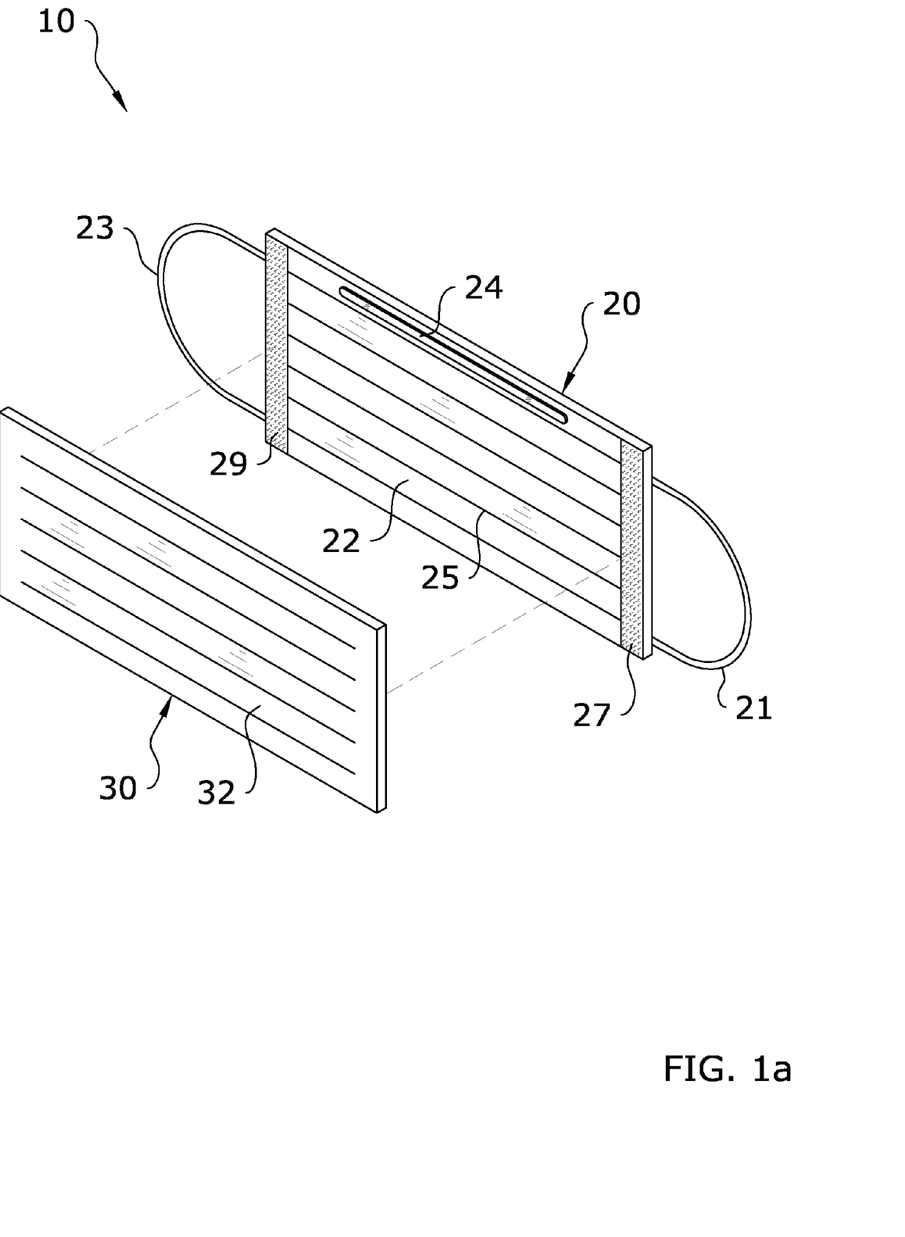
FIG. 1a is a front exploded upper perspective view of a first embodiment of the present invention utilizing a rectangular type of face mask and a removable medicated cover (nighttime model).
Figure 1B:
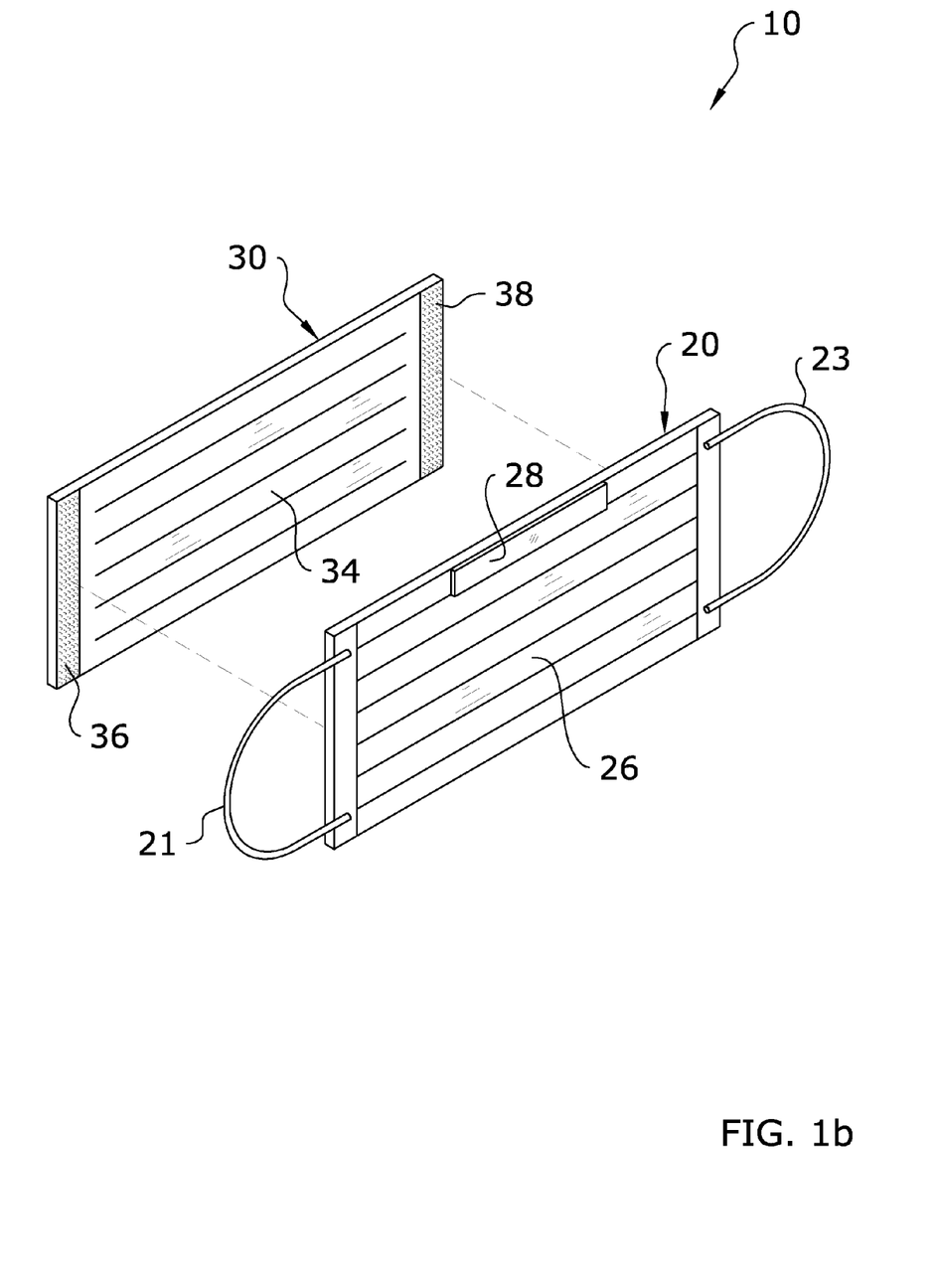
FIG. 1b is a rear exploded upper perspective view of a first embodiment of the present invention utilizing a rectangular type of face mask and a removable medicated cover (nighttime model).
Figure 2:
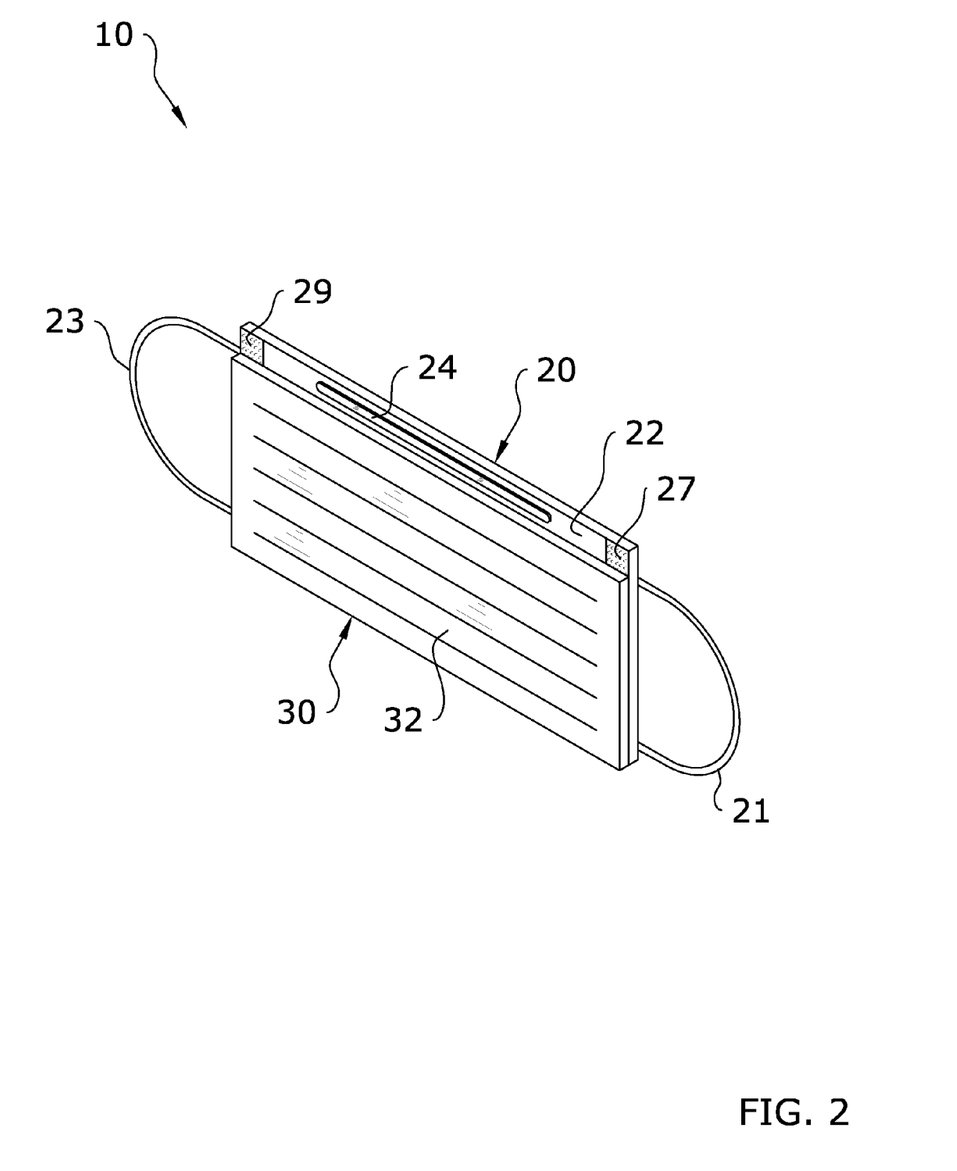
FIG. 2 is a front upper perspective view of the first embodiment (nighttime model).
Figure 3:
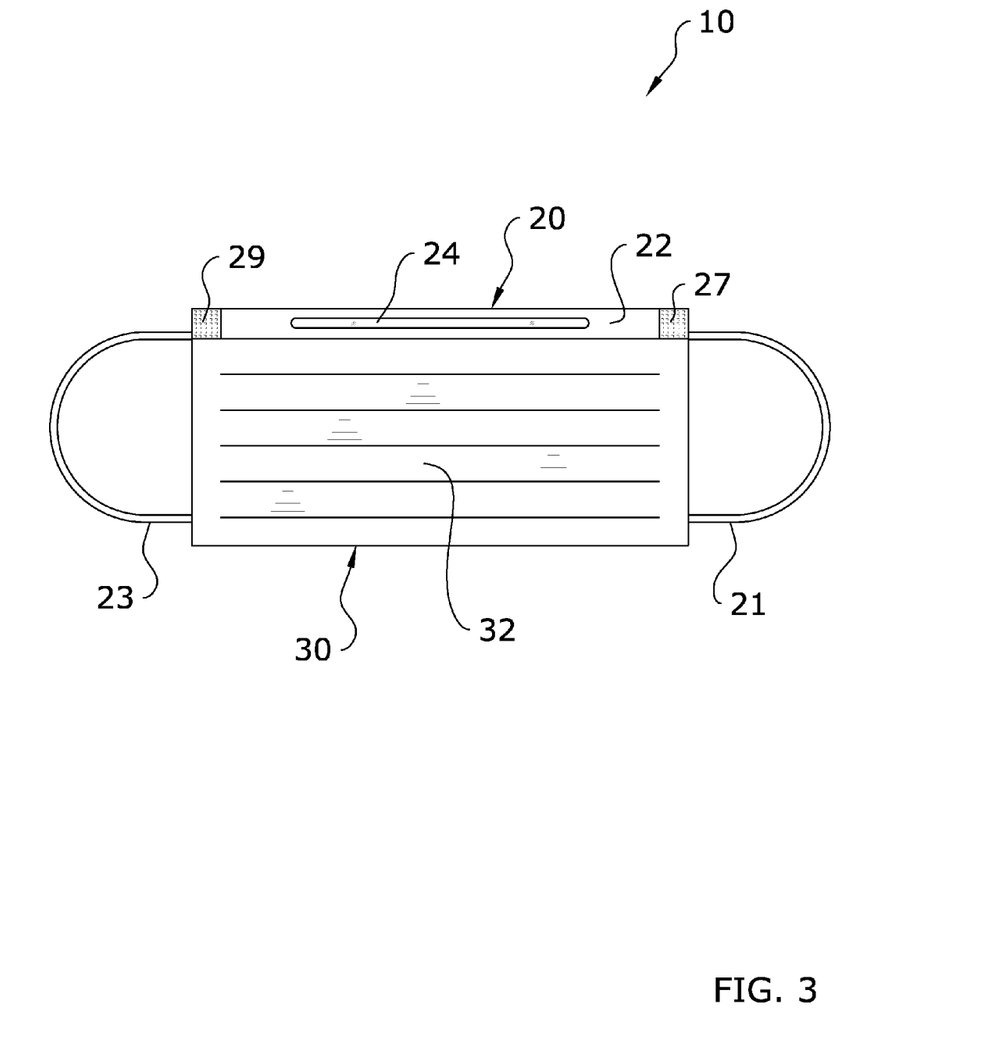
FIG. 3 is a front view of the first embodiment (nighttime model).
Figure 8A:
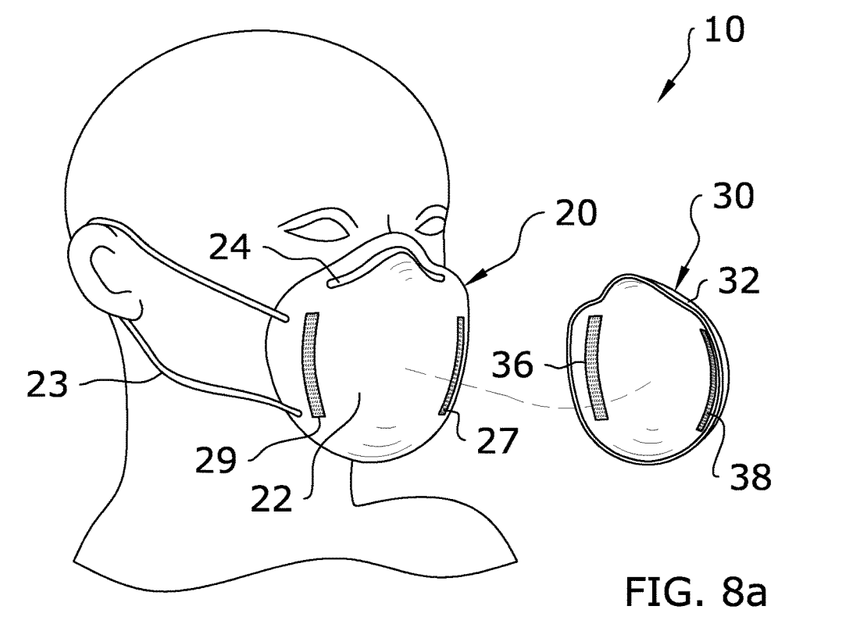
FIG. 8a is a front exploded upper perspective view of a second embodiment of the present invention utilizing a bowl-type of face mask and a removable medicated cover (nighttime model).

FIGS. 1a, 1b, and 8a illustrate exemplary face masks 20 suitable for usage with respect to the present invention. The face mask 20 may be comprised of any mask adapted to be worn upon a face of a user that prevents the passage of germs (viruses and bacteria). The face mask 20 has a size and shape designed for the user. Hence the face mask 20 may have an adult size and also a pediatric size which is smaller than the adult size for younger users.

FIGS. 1a and 1b illustrate a "rectangular-shaped" face mask 20 having a plurality of pleats 25 which is commonly utilized in the medical industry. The plurality of pleats 25 (or folds) allows for the expansion of the face mask 20 so the face mask 20 covers the face of the user from the nose to under the chin of the user. FIG. 8a illustrates a bowl shaped face mask 20 that has a bowl shape that conforms to the face of the user.

The face mask 20 is preferably constructed of a disposable structure and material. The face mask 20 may be comprised of plurality of layers of material such as but not limited to a 3-ply type of face mask 20 wherein the first ply is comprised of a non-woven material such as carded cotton and creped tissue wadding, wherein the second ply is comprised of a non-woven melt blown polypropylene material and wherein the third ply is comprised of a non-woven thermo bond polypropylene material. U.S. Pat. No. 5,467,765 to Maturaporn illustrates an exemplary face mask 20 suitable for usage within the present invention and is hereby incorporated by reference herein. It is preferable, anyhow, to utilize a face mask 20 comprised of a one layer of material to allow for easier breathing when the medicated cover is attached.

The face mask 20 includes an outer surface 22 and an inner surface 26 opposite of the outer surface 22 as illustrated in FIGS. 1a, 1b and 8a of the drawings. The inner surface 26 is positionable facing the face of the user and the outer surface 22 extends away from the face of the user when attached to the head of the user.

Currently, there are four conventional systems for securing a conventional face mask 20 upon the face of a user: ear loops, tie on straps, head band and adhesive strips 28. FIGS. 1a through 5, 8a through 9b illustrate the usage of a left ear loop 21 attached to a left side of the face mask 20 that is positioned about the left ear of the user and a right ear loop 23 attached to a right side of the face mask 20 that is positioned about the right ear of the user. The left ear loop 21 and the right ear loop 23 are comprised of string like material that is preferably elastic. The tie on straps are simply four straps that are tied behind the head of the user. The head band is comprised of an elastic strap that is positioned behind the head. Finally, a no-strap design comprised of non-irritant adhesive attached to the perimeter (a portion of the perimeter or the entire perimeter) of the inner surface 26 of the face mask 20 that is attached to the skin of the user provides an airtight seal that prevents air from leaking about the sides of the face mask 20.

FIG. 1a illustrates a malleable metallic nose piece 24 attached to the outer surface 22 of the face mask 20 that is deformable to the shape of the nose of the user. FIG. 1b illustrates an adhesive strip 28 attached to the inner surface 26 of the face mask 20 opposite of the non-irritant nose piece 24 that adhesively attaches to the nose of the user to provide for a secure and leak-proof attachment about the nose of the user.

C. Medicated Cover.

As illustrated in FIGS. 1a through 8c of the drawings, the medicated cover 30 is formed to fit upon and removably attach to the face mask 20. The medicated cover 30 may have one or more colors and/or aesthetic designs to increase the visual appearance of the medicated cover 30. The medicated cover 30 preferably does not significantly obstruct the flow of air since the face mask 20 preferably filters the air of germs. The medicated cover 30 is comprised of a material that allows for the passage of air (e.g. materials utilized in the face mask 20) and that includes the medication to be dispensed to the user via inhalation therapy (a.k.a. aromatherapy). The medicated cover 30 may have a pleated structure similar to the face mask 20 to allow for forming/expansion to the shape and size of the face of the user. The medicated cover 30 is replaceable and is preferably encased in a sealed package to prevent the release of the medication prior to usage. The user removes the medicated cover 30 from the sealed package to allow for attachment to the face mask 20.

The medicated cover 30 includes a first surface 32 and a second surface 34 opposite of the first surface 32 as illustrated in FIGS. 1a and 1b of the drawings. The second surface 34 of the medicated cover 30 is removably attached to the outer surface 22 of the face mask 20 as shown in FIGS. 2, 4b, 7 and 8b of the drawings.

The medicated cover 30 is preferably approximately the same shape and size as the face mask 20 such that the medicated cover 30 substantially covers the face mask 20. FIGS. 1a and 1b illustrate a rectangular-shaped medicated cover 30 that corresponds to a rectangular shaped face mask 20. FIGS. 8a through 8c illustrate a bowl-shaped medicated cover 30 that corresponds to a bowl-shaped face mask 20. It is preferable that the medicated cover 30 not cover the entire outer surface 22 of the face mask 20 and preferably does not extend completely to the upper edge of the face mask 20 thereby leaving an upper portion of the face mask 20 exposed to allow for the deflectors to extend from the face mask 20 as best illustrated in FIGS. 2, 3, 4a, 5, 7, 8b and 8c of the drawings.

One or more fasteners 27, 29, 36, 38 are utilized to removably attach the medicated cover 30 to the face mask 20. It is preferable that a first mask fastener 27 is attached to the outer surface 22 of the face mask 20 and a first cover fastener 36 is attached to the second surface 34 of the medicated cover 30, wherein the first mask fastener 27 is removably attached to the first cover fastener 36 as illustrated in FIGS. 1a and 1b of the drawings. In addition, a second mask fastener 29 is preferably attached to the outer surface 22 of the face mask 20 and a second cover fastener 38 is preferably attached to the second surface 34 of the medicated cover 30, wherein the second mask fastener 29 is removably attached to the second cover fastener 38. The fasteners 27, 29, 36, 38 are comprised of a hook and loop fasteners, an adhesive tape or any other suitable fastener that allows for removable attachment of the medicated cover 30. Removable attachment of the medicated cover 30 allows for replacement of the medicated cover 30 after the medication within the medicated cover 30 has dissipated to a level wherein the user is not receiving a significant portion of medication as needed. Also, the medicated cover 30 can be replaced when the user needs to use another medicated cover 30 with a different medication or scenting material.

The first mask fastener 27 is preferably attached to a left side of the face mask 20 in a vertical manner and the second mask fastener 29 is attached to a right side of the face mask 20 in vertical manner as illustrated in FIGS. 1a and 8a of the drawings. The first cover fastener 36 is preferably attached to a left side of the medicated mask in a vertical manner and the second cover fastener 38 is attached to a right side of the medicated cover 30 in vertical manner as illustrated in FIGS. 1b and 8a of the drawings.

The medicated cover 30 includes a medication material and/or scenting material that is attached to the first surface 32 and/or the second surface 34 of the medicated cover 30. The medicated cover 30 may also be impregnated with the medication and/or scenting material. The medication provides temporarily medical relief to the user from an illness such as a flu or cold. The scenting material provides comfort to the wearer when encountering undesirable odors.

D. Medicated Strips.

Figure 9A:
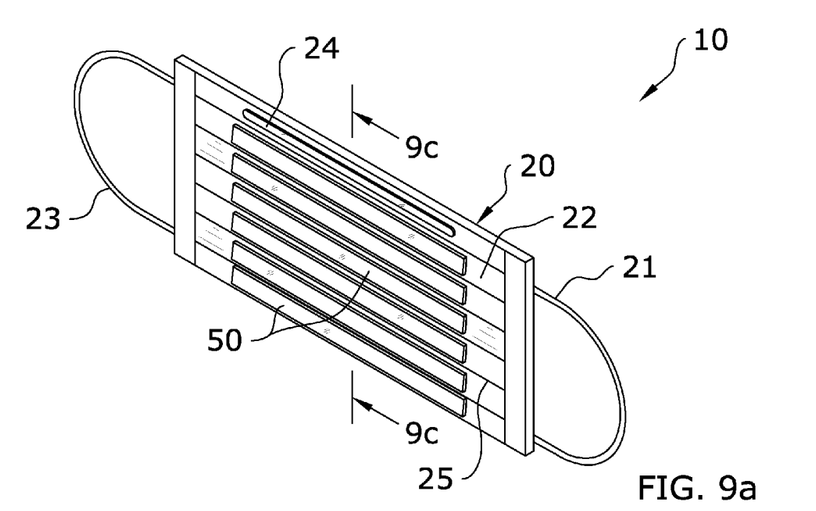
FIG. 9a is a front upper perspective view of a third embodiment of the present invention having a plurality of medicated strips attached to the face mask (nighttime model).
Figure 9B:
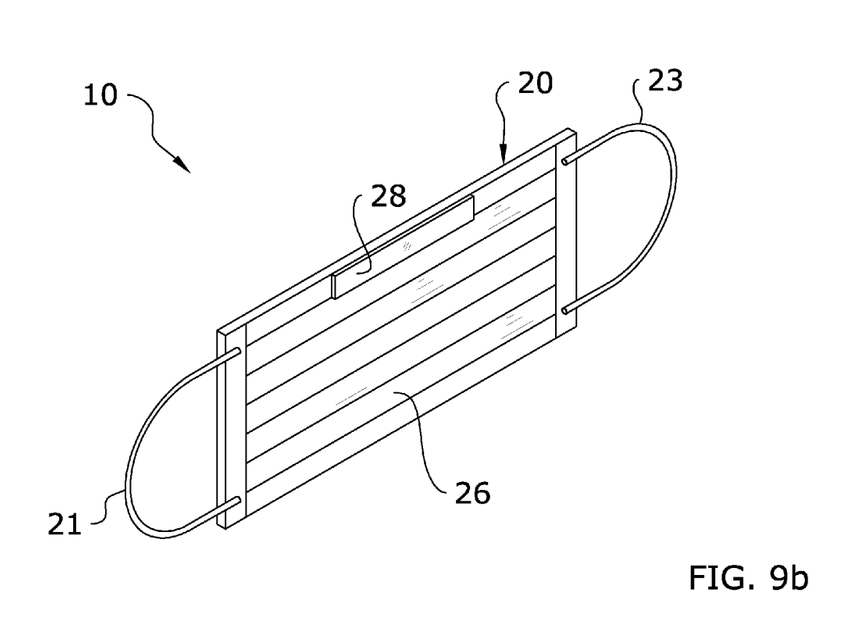
FIG. 9b is a rear upper perspective view of the third embodiment (nighttime model).
Figure 9C:
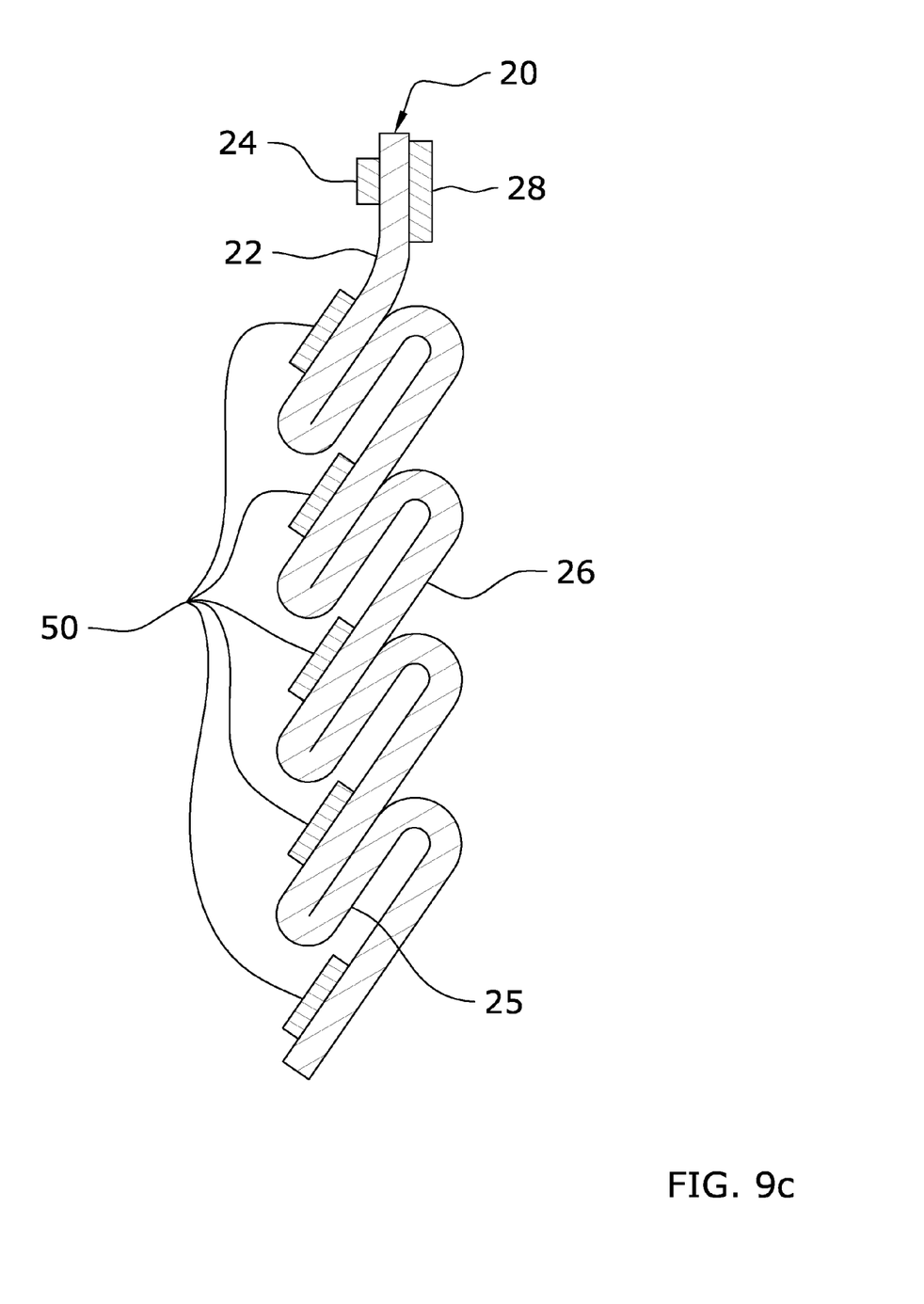
FIG. 9c is a cross sectional view taken along line 9c-9c of FIG. 9a (nighttime model).
Figure 10A:
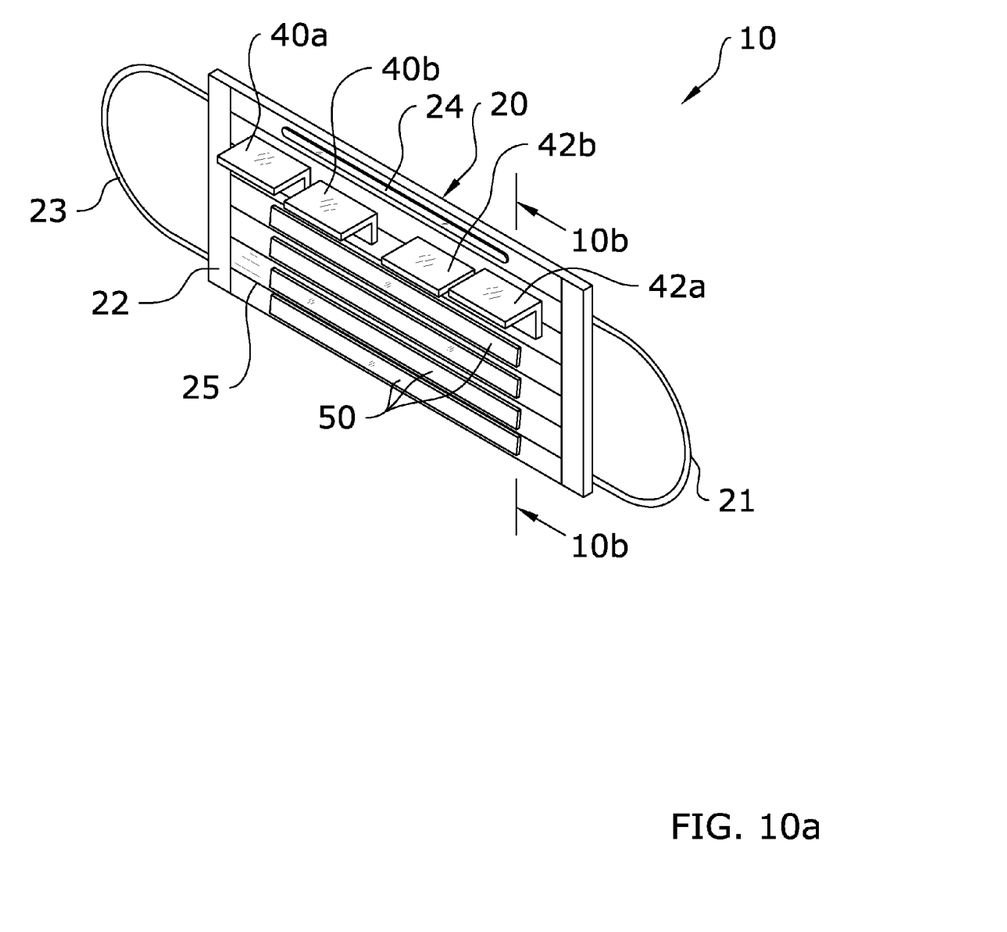
FIG. 10a is a front upper perspective view of the third embodiment with deflectors attached to the face mask (daytime model).
Figure 10B:
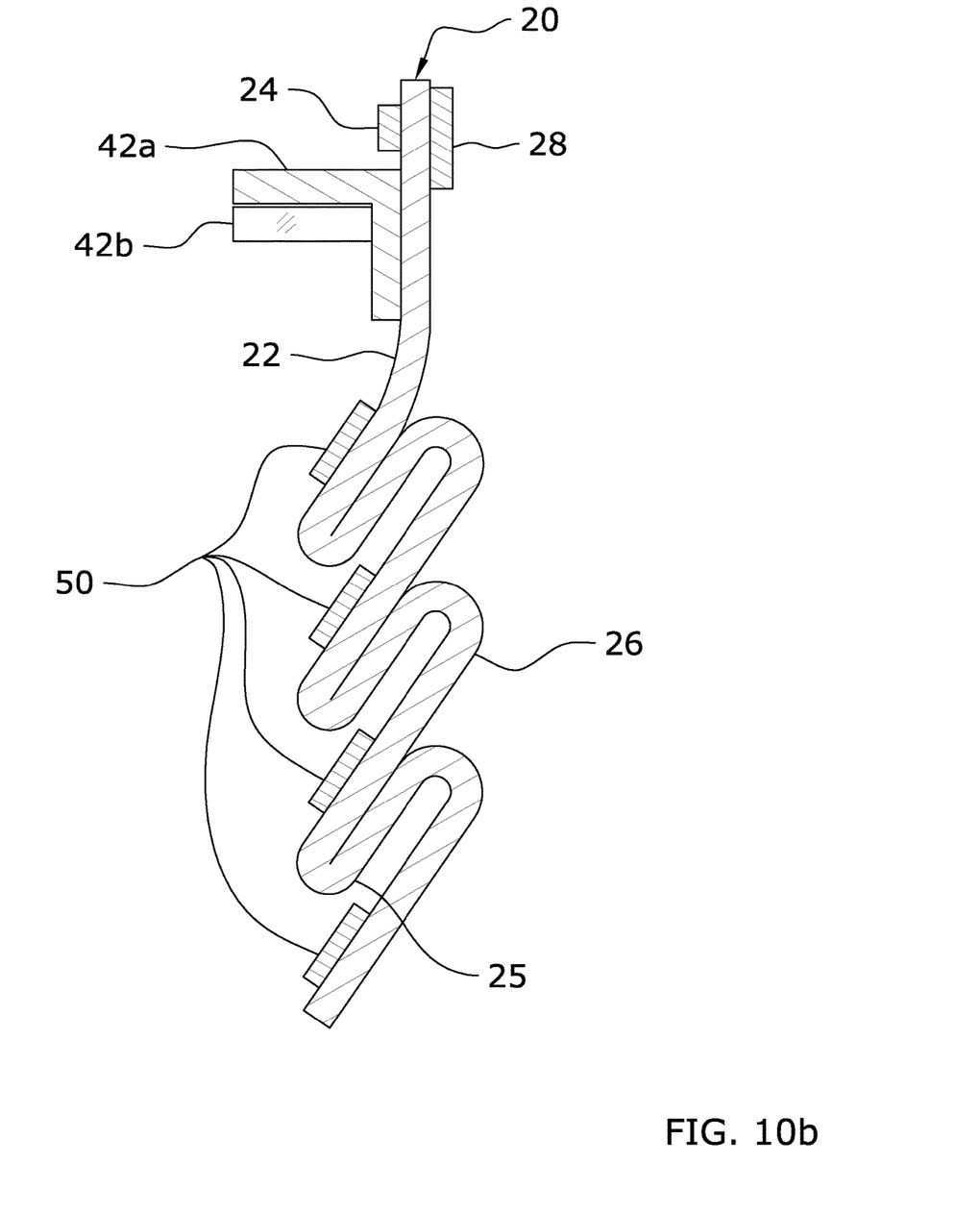
FIG. 10b is a cross sectional view taken along line 10b-10b of FIG. 10a (daytime model).

FIGS. 9a through 10b illustrate a plurality of medicated strips 50 attached to the outer surface 22 of the face mask 20. The medicated strips 50 are preferably elongated and narrow to limit the obstruction of airflow through the face mask 20 as illustrated in FIG. 9a. The plurality of medicated strips 50 preferably extend along a horizontal path and are preferably parallel to one another as further illustrated in FIG. 9a of the drawings. The mediated strips preferably extend along a substantial portion of the width of the face mask 20 as shown in FIG. 9a of the drawings. As shown in FIG. 9c of the drawings, the medicated strips 50 preferably are attached to a lower portion of each of the pleats 25 in the face mask 20 and positioned on the outermost portion of the pleats 25. The whole face mask 20 is preferably stored within a sealed packaging to prevent the dissipation of the medication prior to usage.

The medicated strips 50 each include a medication that is transmitted to the respiratory track of the user via airborne transmission. The medication preferably provides relief of cold and flu symptoms such as coughs and congestion or any other symptoms that may be relieved by aromatherapy. The medication utilized within the medicated strips 50 may be comprised of the same medication that the medicated cover 30 is impregnated with. The medicated strips 50 may also be attached to the first surface 32 of the medicated cover 30 to dispense the medication for the medicated cover 30. More than one medication can be utilized on different medicated strips 50 of the same face mask 20 or medicated cover 30.

E. Air Transmissible Material (Medication Material and/or Scenting Material).

For the purposes of discussion, the air transmissible material (medication material and/or scenting material) will be discussed as being applied to the medicated cover 30, whereas it can be appreciated that the air transmissible material may be applied the same to the medicated strips 50. The medication is transmitted to a respiratory track of the user via airborne transmission and preferably provides relief of cold and flu symptoms. Scenting materials are also transmitted to the respiratory track of the user via airborne transmission to provide a desirable scent to the user that masks external odors or simply provides a desirable scent to the user. Utilizing inhalation therapy, the medicated cover 30 dispenses medication to the user via airborne transmission when the user breathes in through the face mask 20 and the medicated cover 30.

The medicated cover 30 preferably provides an aromatic vapor that is released and breathed in through the face mask 20 by the user. The medication utilized within the medicated cover 30 may be comprised any aromatherapy that provides temporary relief of cold and flu symptoms (e.g. nasal and sinus congestion) or any other symptoms that may be relieved by aromatherapy. In one embodiment of the present invention, the medication is comprised of a nasal decongestant embodied in a vapor that is inhaled by the user thereby providing temporary relief to the user. The medicated cover 30 and medicated strips 50 may be comprised of vapor pads impregnated with menthol that release relieving menthol vapors gradually to the user to provide breathing comfort to the user experiencing a cold or flu.

PROCTER & GAMBLE COMPANY in Cincinnati, Ohio manufactures a line of products under the trademark VICKS® that dispense an aroma, alcohol and liniments (e.g. VAPORUB®, VAPOPADS®) that are suitable for usage within the present invention. U.S. Publication No. 2005/0249693 filed by Rau discloses various compositions suitable for usage as medication within the present invention and is hereby incorporated by reference.

D. Deflector.

If the medication utilized on the medicated cover 30 or the medicated strips 50 is a potential irritant to the eyes (e.g. menthol vapors), a daytime version of the present invention is preferably utilized to limit the amount of medication vapor that makes contact with the eyes. In the daytime version, deflectors 40, 42 are attached to the upper portion of the outer surface 22 of the face mask 20 as illustrated in FIGS. 5, 6, 7, 8c, 10a and 10b of the drawings. The deflectors 40, 42 are preferably comprised of a transparent material so as to not interfere with the downward vision of the user, however, non-transparent or semi-transparent materials may be utilized optionally. The deflectors extend outwardly from the face mask 20 to reduce the volume of airflow containing the medication vapor that engages eyes of the user from the medicated cover 30 or the medicated strips 50.

Figure 6:
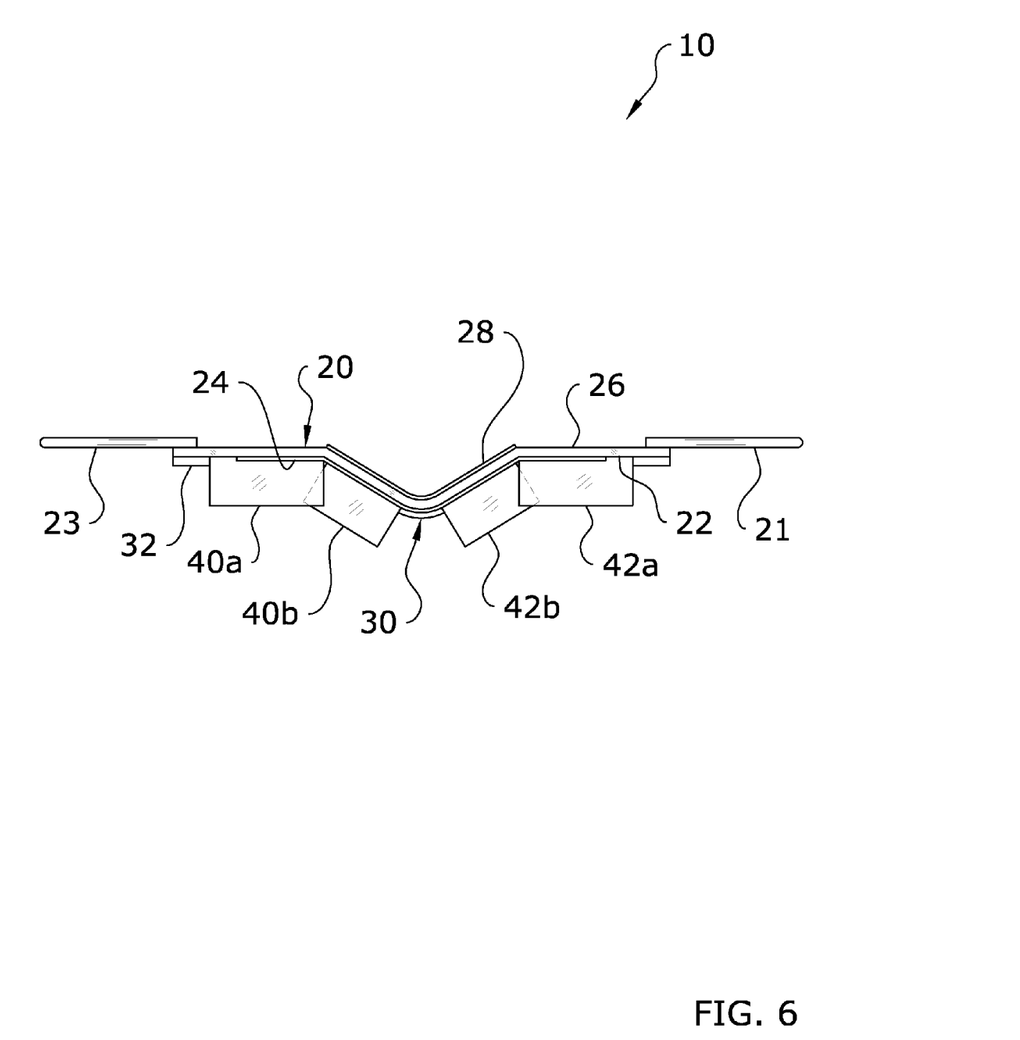
FIG. 6 is a top view of the first embodiment with deflectors (daytime model).

FIGS. 5, 6, 7, 8c, 10a and 10b of the drawings illustrate the usage of a plurality of deflectors 40, 42. A plurality of right deflectors 40 are preferably attached to a right portion of the face mask 20 and a plurality of left deflectors 42 are preferably attached to a left portion of the face mask 20. The right deflectors 40 are positioned on the right side of the face mask 20 and the left deflectors 42 are positioned on the left side of the face mask 20 as illustrated in FIG. 6 of the drawings.

Figure 7:
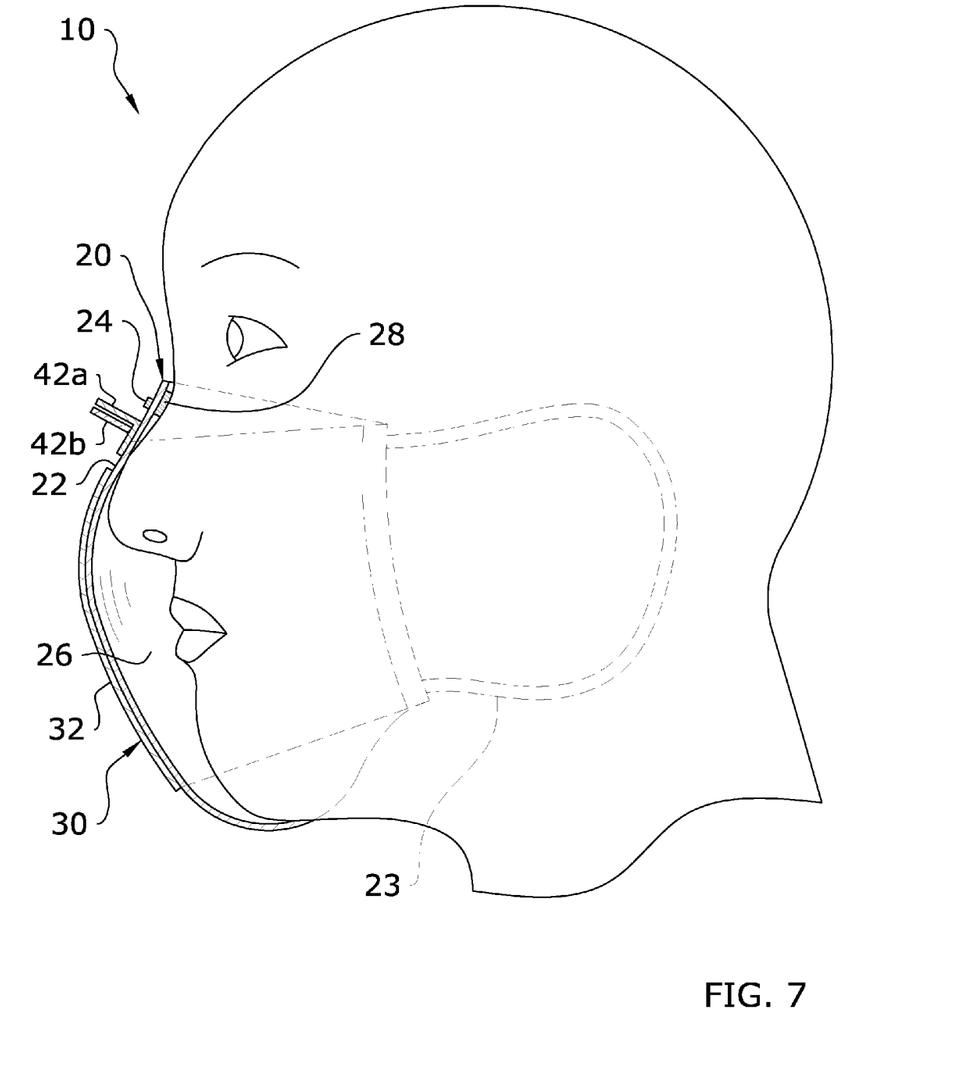
FIG. 7 is a cross sectional view taken along line 7-7 of FIG. 5 (daytime model).
Figure 8B:
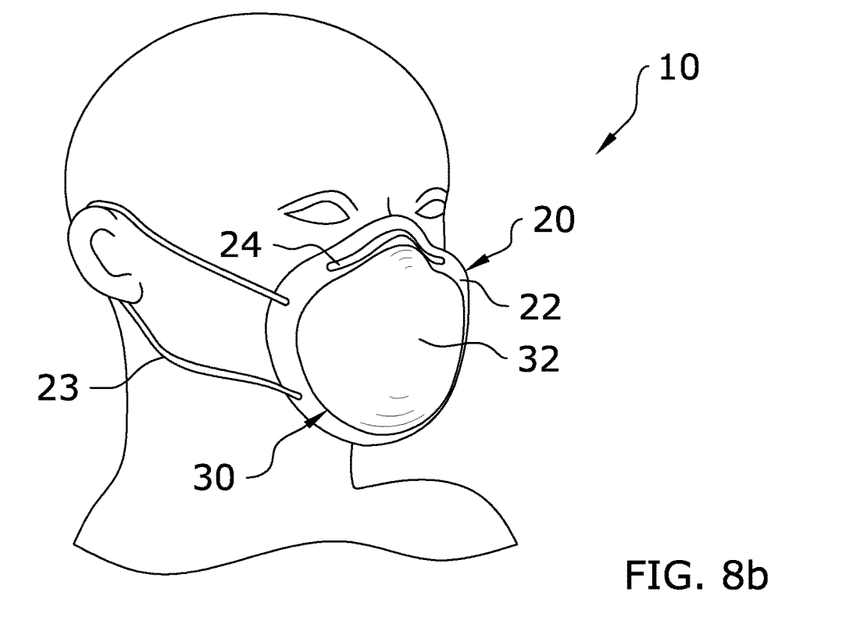
FIG. 8b is a front upper perspective view of the second embodiment being worn by a user (nighttime model).
Figure 8C:
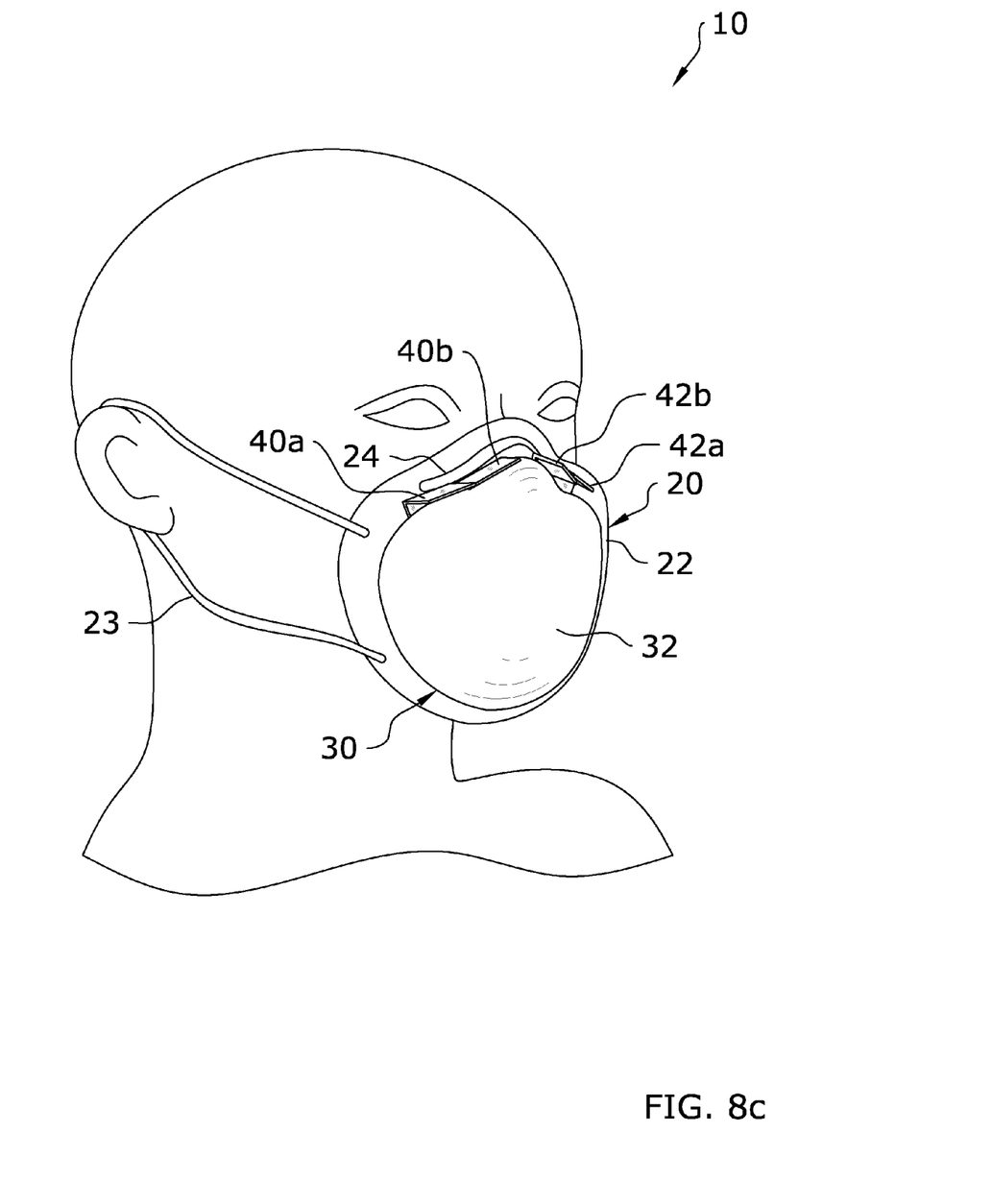
FIG. 8c is a front upper perspective view of the second embodiment with deflectors attached to the face mask (daytime model).

The deflectors 40, 42 preferably have an inverted L-shape that has a base portion attached parallel to the outer surface 22 of the face mask 20 and an extended portion that extends outwardly from the outer surface 22 of the face mask 20 as best illustrated in FIG. 7 of the drawings. The deflectors 40, 42 preferably extend outwardly at least 0.5 inches to protect the eyes of the user.

It is preferable to have a pair of right deflectors 40 adjacent to each other and a pair of left deflectors 42 adjacent to each another as best illustrated in FIG. 6 of the drawings. As further shown in FIGS. 6 and 7 of the drawings, one of the right deflectors 40 is slightly lower to allow for overlapping of the right deflectors 40 and one of the left deflectors 42 is slightly lower to allow for overlapping of the left deflectors 42. The overlapping of the deflectors 40, 42 allows for the face mask 20 to conform and change to the shape of the user's face without retaining a static shape that would be encountered with a single deflector extending across the entire face mask 20.

F. Operation.

Figure 4A:
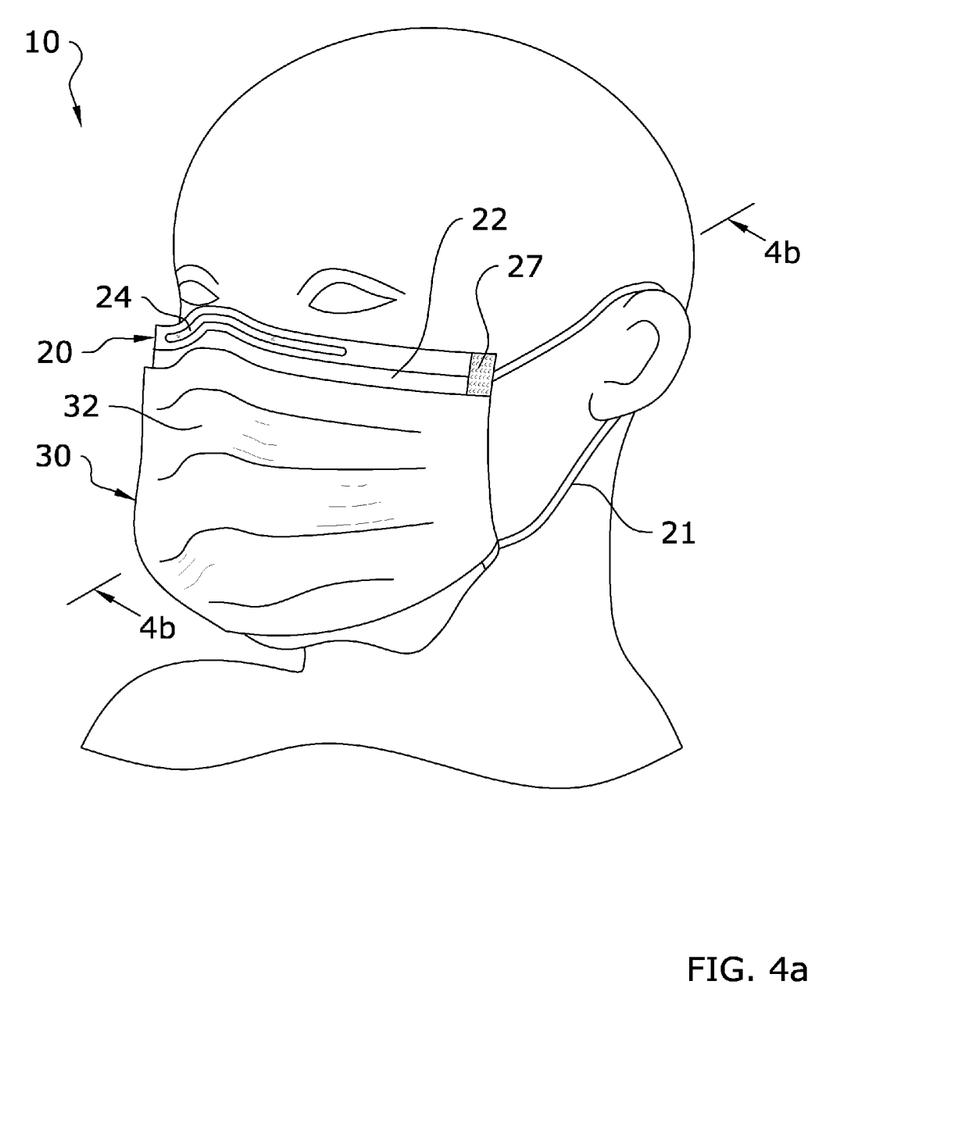
FIG. 4a is a front perspective view of the first embodiment being worn by a user (nighttime model).
Figure 4B:
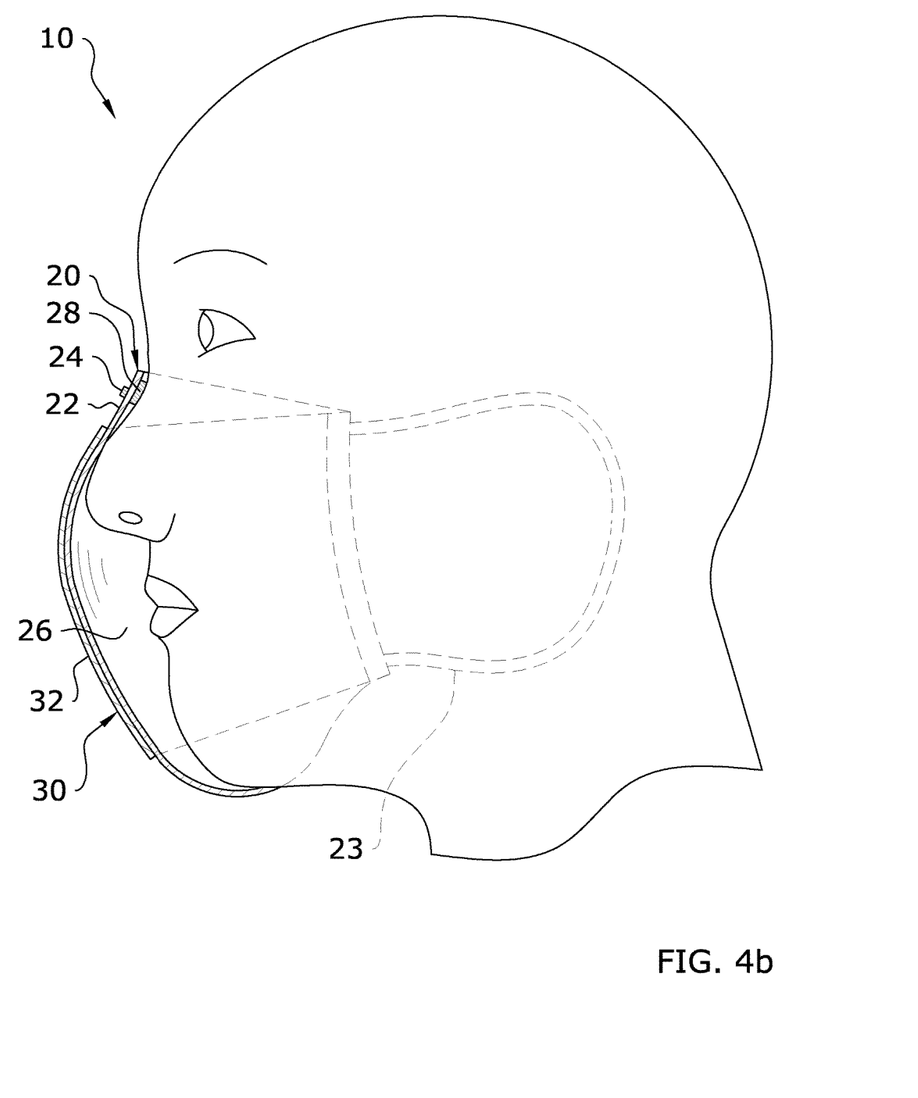
FIG. 4b is a cross sectional view taken along line 4b-4b of FIG. 4a (nighttime model).
Figure 5:
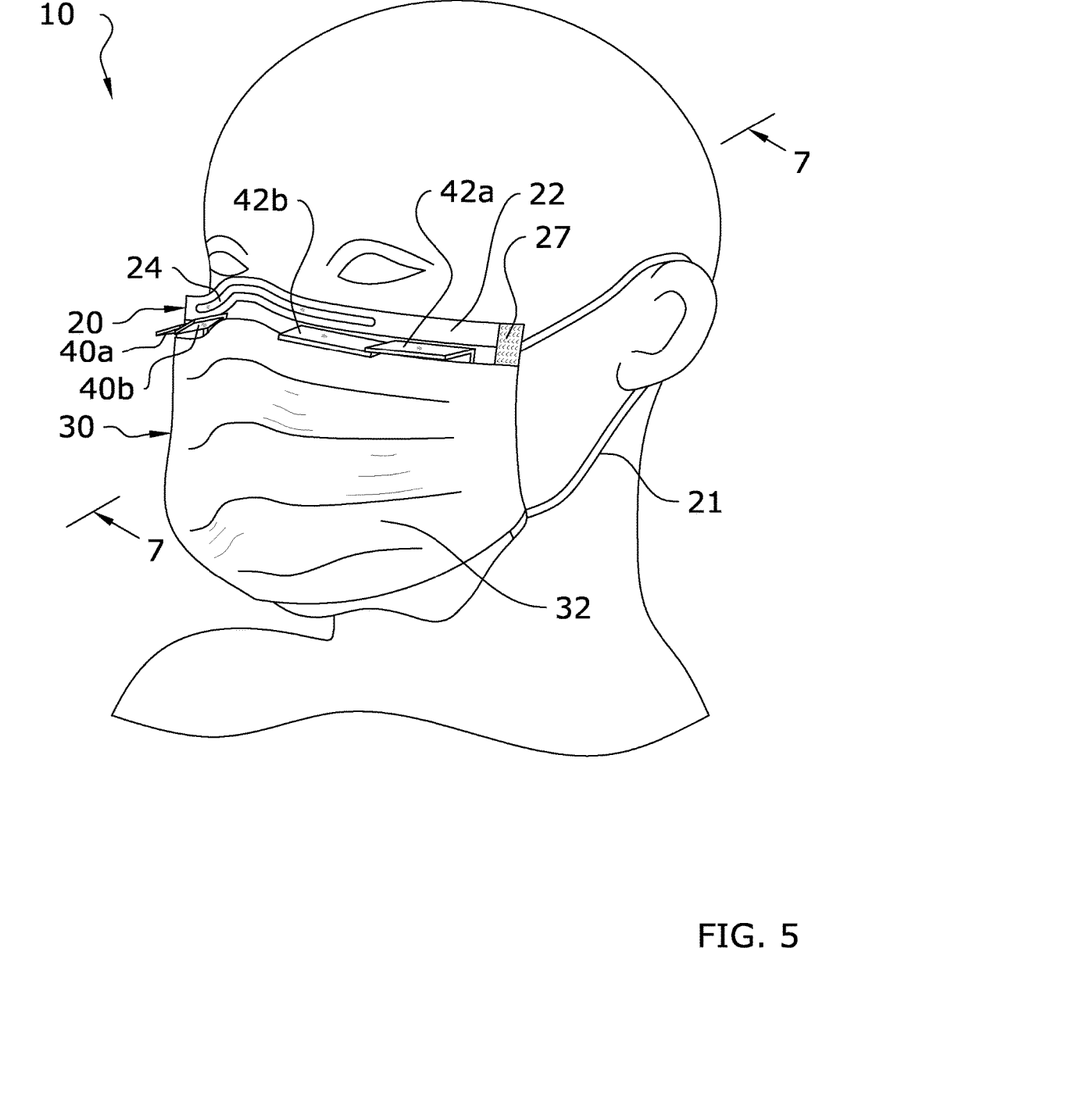
FIG. 5 is a front perspective view of the first embodiment with deflectors attached to the face mask (daytime model).

In use, the user positions and secures the face mask 20 upon their face as illustrated in FIGS. 4a and 8a of the drawings. The user then removes the medicated cover 30 from the sealed packaging and aligns the fasteners 36, 38 of the medicated cover 30 with the fasteners 27, 29 of the face mask 20 and then removably attaches the medicated cover 30 to the face mask 20. It can be appreciated that the medicated cover 30 may be attached to the face mask 20 prior to attaching the face mask 20 to the head of the user. In use, the user wears the face mask 20 to prevent the transmission of germs with the medication being inhaled by the user thereby providing temporary relief from a cold or the flu. If the medication within the medicated cover 30 begins to lose its level of medical effectiveness which will occur after a period of time, the user removes the medicated cover 30 from the face mask 20 and attaches a new medicated cover 30 to the face mask 20 to continue the aromatherapy treatment. At daytime, the deflectors 40, 42 reduce of the amount of medication vapor that passes upwardly from the body heat and/or exhaling of the user to the eyes of the user.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A medicated face mask system, comprising:
   a face mask adapted to be worn upon a face of a user, wherein said face mask includes an outer surface and an inner surface opposite of said outer surface, wherein said inner surface is positionable facing the face of the user; and
   at least one deflector having a base portion and an extended portion, a cross section of said at least one deflector is substantially L-shaped, said extended portion extends outward from said base portion, said base portion is attached to said outer surface of said face mask and is substantially parallel thereto, wherein said at least one deflector reduces airflow to eyes of the user, said at least one deflector is comprised of a plurality of right deflectors attached to a right portion of said face mask and a plurality of left deflectors attached to a left portion of said face mask.

2. The medicated face mask system of claim 1, comprising:
   a medicated cover having a first surface and a second surface opposite of said first surface, wherein said second surface of said medicated cover is removably attached to said outer surface of said face mask, wherein said medicated cover includes a medication, wherein said medication is transmitted to a respiratory track of the user via airborne transmission, wherein said medication provides relief of cold symptoms.

3. The medicated face mask system of claim 2, wherein said medication is comprised of a nasal decongestant.

4. The medicated face mask system of claim 2, wherein said medicated cover is approximately the same shape and size as said face mask such that said medicated cover substantially covers said face mask.

5. The medicated face mask system of claim 2, including a first mask fastener attached to said outer surface of said face mask, a first cover fastener attached to said second surface of said medicated cover, wherein said first mask fastener is removably attached to said first cover fastener, a second mask fastener attached to said outer surface of said face mask and a second cover fastener attached to said second surface of said medicated cover, wherein said second mask fastener is removably attached to said second cover fastener.

6. The medicated face mask system of claim 5, wherein said fasteners are comprised of a hook and loop fasteners or an adhesive tape, and wherein said first mask fastener is attached to a left side of said face mask and wherein said second mask fastener is attached to a right side of said face mask.

7. The medicated face mask system of claim 2, wherein said face mask is rectangular-shaped or bowl-shaped.

8. The medicated face mask system of claim 1, including a plurality of medicated strips attached to said outer surface of said face mask, wherein said medicated strips each include a medication, wherein said medication is transmitted to a respiratory track of the user via airborne transmission, wherein said medication provides relief of a symptom that can be relieved by aromatherapy.

* * * * *